(12) United States Patent
Cheiky et al.

(10) Patent No.: US 6,929,884 B2
(45) Date of Patent: Aug. 16, 2005

(54) METHOD FOR MANUFACTURE OF FILMS CONTAINING INSOLUBLE SOLIDS EMBEDDED IN CELLULOSE-BASED FILMS

(75) Inventors: Michael Cheiky, Thousand Oaks, CA (US); Wilson Hago, Ventura, CA (US)

(73) Assignee: Zinc Matrix Power, Inc., Santa Barbara, CA (US)

( * ) Notice: Subject to any disclaimer, the term of this patent is extended or adjusted under 35 U.S.C. 154(b) by 394 days.

(21) Appl. No.: 10/246,515

(22) Filed: Sep. 18, 2002

(65) Prior Publication Data

US 2005/0104247 A1    May 19, 2005

Related U.S. Application Data

(63) Continuation-in-part of application No. 09/839,871, filed on Apr. 19, 2001, now Pat. No. 6,558,849, and a continuation-in-part of application No. 09/839,327, filed on Apr. 19, 2001, now Pat. No. 6,682,854, and a continuation-in-part of application No. 09/839,320, filed on Apr. 19, 2001, now Pat. No. 6,541,160.

(51) Int. Cl.$^7$ .......................... H01M 2/16; D01F 2/00; D01F 2/24; C08B 3/00; C08B 16/00
(52) U.S. Cl. ...................... 429/255; 429/247; 429/248; 429/249; 429/251; 29/623.1; 264/187; 264/207; 536/30; 536/56; 536/57
(58) Field of Search ................................ 429/255, 247, 429/248, 249, 251; 29/623.1; 264/187, 207; 536/30, 56, 57

(56) References Cited

U.S. PATENT DOCUMENTS 4,367,191 A * 1/1983 Cuculo et al. .............. 264/187

* cited by examiner

*Primary Examiner*—Patrick Joseph Ryan
*Assistant Examiner*—Angela J. Martin
(74) *Attorney, Agent, or Firm*—Marvin E. Jacobs

(57) ABSTRACT

A film which slowly releases solids is prepared by dissolving cellulose in a solvent such as an alkali metal salt, for example $L_1Cl$ in a polar solvent such as DMAC, dispersing the solid in the solution and gelling the solution with water to form a film.

32 Claims, No Drawings

METHOD FOR MANUFACTURE OF FILMS CONTAINING INSOLUBLE SOLIDS EMBEDDED IN CELLULOSE-BASED FILMS

CROSS-REFERENCE TO RELATED APPLICATION

This application is a continuation-in-part of Ser. No. 09/839,871, now U.S. Pat. No. 6,558,849, Ser. No. 09/839,320, now U.S. Pat. No. 6,541,160, and Ser. No. 09/839,327, now U.S. Pat. No. 6,682,854 all filed Apr. 19, 2001.

TECHNICAL FIELD

This invention relates to a method of making cellulose-based films containing insoluble substances.

BACKGROUND OF THE INVENTION

There is a need for controlled release of substances in a variety of fields. One example of this is in the medical field where there is the need to time release ingested or injected drugs. There are several ways to effect the controlled and extended release of substances, such as through the use of matrix tablets, micro-capsules or coated pellets that are incorporated into hard gelatin capsules or enteric coated labels. Production processes include conventional granulation and tabletting of matrix tablets, pan coating, prilling, extrusion and spheroidization, fluid bed processes, spray drying, spray chilling, and coacervation.

In most controlled release devices, the active substance is surrounded by a polymer matrix which slowly dissolves on contact with aqueous media to release the active substance.

STATEMENT OF THE PRIOR ART

In U.S. Pat. No. 6,096,834 the active material is crosslinked to the polymer matrix and the controlled release is achieved by a slow hydrolysis of this linkage. Water soluble solids were added to a nonwoven web of fibrous cellulosic material in order to confer flame retardancy in U.S. Pat. No. 5,912,196. In the textile field, alkali metal additives were added to Spandex® fabric in U.S. Pat. No. 5,539,037 in a concentration range 0.02–0.25% in order to increase the heat efficiency of the Spandex® fabric.

Wan in U.S. Pat. No. 5,846,213 discloses a method for making a film from microbially produced cellulose, particularly cellulose produced from the culture of Acetobacter xylinum in a stirred tank. The film is made by dissolving the cellulose in a solvent system comprising dimethylacetamide and lithium chloride, casting the resulting solution onto a flat surface and regenerating the film in a gelatin bath. A humectant can be incorporated into the film by solvent exchange.

Though active molecules have been encapsulated in a cellulose matrix in a wide variety of applications, these techniques have relied mostly on granulation and tabletting technologies.

STATEMENT OF THE INVENTION

It is desirable to have a matrix where the active material experiences a substantial barrier to diffusion, as in the case where the matrix is cohesive at the molecular level. The present invention discloses a method for making doped membranes from a wide variety of celluloses, said films having the characteristic of very slow leaching of the insoluble solid. Cellulose membranes are particularly useful in a variety of applications. They are useful as battery separators and dialysis membranes. Their similarity to the human skin has made them useful as wound dressings. It is useful to dope polymers with different solids in order to effect a change in a certain property. The present invention provides a method for manufacturing cellulose-based membranes that contain insoluble solids, with a solubility less than 1 mg/L and less than 50% solids by weight of cellulose. It is known that various celluloses can be dissolved in a wide variety of solvents. Among the solvents that dissolve cellulose without significant degradation is a combination of an alkali metal salt such as lithium chloride with a polar solvent such as dimethylacetamide. This solvent is able to dissolve a wide variety of celluloses. Celluloses with a degree of polymerization from 200 to 1200, in the form of, but not limited to, microcrystalline cellulose, cotton fiber, paper and microgranular cellulose can be dissolved in a solvent containing 3 to 8% by wt alkali metal salt to polar solvent and 1 to 11% wt cellulose to polar solvent. The incorporation of the solids in the membrane is achieved by mixing the insoluble solids in a cellulose solution of an alkali metal salt such as LiCl in a polar solvent such as DMSO, DMF, suitably dimethylacetamide (DMAC), casting said solution under controlled environmental conditions until a gel is formed, rinsing said gel until all LiCl and polar solvent are removed, and drying this gel. This method produces a uniform dispersion of a solid in a film that has a substantial barrier to diffusion of the solid out of the film.

The present invention teaches the encapsulation of a wide variety of solids having low solubility in water, generally less than 1 mg/L. The insoluble solids may be added to the solution to produce a membrane that exhibits a uniform distribution of the solids. Because the cellulose membrane formed from the solution is cohesive at the molecular level, the retained encapsulated solids are subject to a polymer matrix having a significant barrier to diffusion, although the solids may slowly be leached out of the polymer matrix in an appropriate liquid environment. The cellulose encapsulated solid is slowly released from the polymer matrix at a rate of 1 ppm/hour to 40 ppm/hour at ambient conditions, where ppm refers to parts per million of the insoluble solid present.

DETAILED DESCRIPTION OF THE INVENTION

Of the solids that may be added, some inorganic salts are more suitable in terms of insolubility. The following illustrative list is not inclusive. Among the candidates are:

Elements: all water insoluble elements
Phosphates: $AlPO_4$
Metaphosphates: $Al(PO_3)_3$
Sulfides: $NaS$, $KS$, $ZnS$, $Bi_2S_3$
Selenides: $As_2Se$
Chromates: $BaCrO_4$
Carbonates: $BaCO_3$
Boride: $BaB_6$
Molybdates: $BaMoO_4$
Niobates: $Ba(NbO_3)_2$, $Cd(NbO_3)_2$
Halides: $AgCl$, $AgBr$, $AgI$, $AgCN$, $CaF_2$
Iodates: $AgIO_3$
Carbonyls: $Mn_2(CO)_{10}$
Oxides: $ZrO_2$, $T_1O_2$ Of the heavy metal oxides, suitable compounds include $ZrO_2$ and $TiO_2$. Suitable dyes include copper pthallocyanine and zinc pthallocyanine.

The concentration of salt should not exceed 50% of the cellulose weight, since at high concentrations of solids cellulose molecular cohesion is poor and no membrane would result. The preferred concentration of salt is from 5–45% by weight, suitably 10–30 percent by weight.

In addition to the salt, a softener, such as glycerol or decane, may be added to the solution, as long as it is soluble in the solvent.

An important aspect of the method is the rate at which water moisture is introduced to coagulate the gel. The introduction of water to the cast mixture cannot be too slow or too fast. If it is too slow, no gel will form in a meaningful amount of time. If it is too fast, the gel formed will not be cohesive and the final film will not be strong. The rate of deposition of water affects the pore size and ultimately affects the leach rate of the entrapped solid. Generally the water is introduced to the solution at a rate from 1 ppm/hr/cm$^2$ to 6000 ppm/hr/cm$^2$, preferably at a rate from 30 ppm/hr/cm$^2$ to 90 ppm/hr/cm$^2$. The solution can be slowly gelled by exposure to ambient, moist, atmosphere.

The solution can be coagulated with conventional techniques, either by exposure to ambient moisture or by direct application of a water stream to the resulting solution. It has been observed that a relative humidity range of 35%–80% at a temperature range of 15 to 30 degrees Celsius yields acceptable gels within a 1 to 3 hour range.

The coagulated cellulose material, in the form of a cohesive gel with entrapped solid, is washed to remove the polar solvent and the salt. It is possible to employ alcohols mixed with water, but it is preferable that they be kept below a 50% volume ratio.

After thorough washing of the resulting gel, the gel may be dried with any conventional technique such as air drying, vacuum drying or press drying.

EXAMPLE 1

100 g of LiCl is dissolved in 2 kg of dimethylacetamide (DMAC) at room temperature. 40 g of microcrystalline cellulose (MCC, Aldrich 31,069-7) is placed in a solution containing 2 kg of LiCl/DMAC solvent and heated to 120 degrees Celsius for 15 minutes. The cooled solution provides a clear solution. The solution is cooled to room temperature and 5.1 g copper pthallocyanine is added to the solution. Deionized water is introduced to form a blue gel at a rate of 40 ppm/hr/cm$^2$. After gelling at 55% relative humidity at 22 degrees Celsius for 2 hours, the blue gel is rinsed with deionized water to remove all solvent and LiCl. The clean gel is placed in a dry-press mount at 105 degrees Celsius for 1.5 hours at which point a bright blue membrane is obtained. This membrane retains its color despite being soaked in water for several days.

EXAMPLE 2

100 g of LiCl is dissolved in 2 kg of dimethylacetamide (DMAC) at room temperature. 40 g of microcrystalline cellulose (MCC, Aldrich 31,069-7) is placed in a solution containing 2 kg of LiCl/DMAC solvent and heated to 120 degrees Celsius for 15 minutes. The cooled solution provides a clear solution. The solution is cooled to room temperature and 3.2 g CaF$_2$ is added to the solution. After gelling with ambient moisture over a period of 3 hours, the gel is rinsed with deionized water to remove all solvent and LiCl. The clean gel is placed in a dry-press mount at 105 degrees Celsius for 1.5 hours at which point a clear hazy film is obtained.

EXAMPLE 3

40 grams of microcrystalline cellulose (MCC, Aldrich 31,069-7) is placed in a solution of 2 kg of 5% LiCl/DMAC and heated to 120 degrees Celsius for 15 minutes. The cooled solution affords a clear solution of MCC. 26.7 grams of ethyl cellulose (EC) is dissolved in 530 ml DMAC separately. The MCC and EC solutions are combined in a 60/40 weight ratio by polymer weight. To this mixture 3.3 g CaF$_2$ is added and stirred for 15 minutes. 40 ml of the combined solution is placed on a glass tray. A humidifier providing water over the glass tray yields a gelled product containing phases of MCC and EC. This gel is then washed with water repeatedly until all DMAC and LiCl are removed. The gel is then dried with a press-dry, affording a film useful as a separator.

EXAMPLE 4

40 grams of microcrystalline cellulose is added to a solution of 2 kg of 5% LiCl/DMAC. The solution is heated to 120 degrees Celsius for 15 minutes. The cooled solution affords a clear solution of microcrystalline cellulose. 26.7 grams of ethyl cellulose is dissolved in 530 ml DMAC separately. The microcrystalline cellulose and the ethyl cellulose solutions are combined in a 60/40 weight ratio by polymer weight. To this mixture 8 g Cu(OH)$_2$ is added and stirred for 15 minutes. 40 ml of the combined solution is placed on a glass tray. A humidifier providing water over the glass tray yields a gelled product containing phases of microcrystalline cellulose and ethyl cellulose. This gel is then washed with water repeatedly until all DMAC and LiCl are removed. The gel is then dried with a press-dry, affording a blue film useful as a battery separator.

EXAMPLE 5

Separators containing 2–25% by weight of a metal sulfide in a cellulose-ethyl cellulose were prepared by the method of Example 4. These separators can be utilized adjacent a separation containing a copper salt as described in copending application Ser. No. 09/839,320, the disclosure of which is expressly incorporated by reference.

It is to be realized that only preferred embodiments of the invention have been described and that numerous substitutions, modifications and alterations are permissible without departing from the spirit and scope of the invention as defined in the following claims.

What is claimed is:

1. A method for the manufacture of a cellulose film containing a dispersion of insoluble solids embedded in said film for use in the controlled release of said solids from said film comprising the steps of:
   dissolving cellulose in a solvent comprising an alkali metal salt and an organic polar solvent to form a cellulose solution;
   adding to the solution solids insoluble in the cellulose solution with mixing to form a uniform dispersion of the said solids in the cellulose solution;
   casting the dispersion to form a gel matrix containing a dispersion of said solids;
   rinsing the gel matrix to remove the alkali metal salt and the organic polar solvent from the gel matrix containing said dispersion of solids; and
   drying the rinsed gel matrix to form a cellulose film containing a dispersion of said solids.

2. A method according to claim 1 wherein the cellulose selected from the group consisting of microcrystalline cellulose, cotton fiber paper and microgranular cellulose.

3. A method according to claim 2 wherein the degree of polymerization of the cellulose is in the range of 200–1200.

4. A method according to claim 1 wherein the salt is lithium chloride, the solvent is dimethylacetamide and the concentration range of lithium chloride to dimethylacetamide is 3–8% by weight.

5. A method according to claim 4 wherein the concentration range of the cellulose to solvent is 1–11% by weight.

6. A method according to claim 1 where in the dispersed solids are released from the gel matrix at a rate of 1 ppm/hour to 40 ppm/hour when the film is in contact with a liquid environment.

7. A method according to claim 1 wherein the solids added to the cellulose solution is selected from a water insoluble element, a dye and a slowly dissolving salt having a solubility in water less than 1 mg/L.

8. A method according to claim 7 wherein the slowly dissolving salt is selected from the group consisting of a phosphate salt, a metaphosphate salt, a sulfide, a chromate, a halide, a cyanide, an iodate, a carbonyl, an oxide, a boride, a molybdate, a carbonate and a niobate.

9. A method according to claim 8 in which the salt is $AlPO_4$.

10. A method according to claim 8 in which the metaphosphate is $Al(PO_3)_3$.

11. A method according to claim 8 wherein the sulfide is selected from the group consisting of NaS, KS, ZnS and $Bi_2S_3$.

12. A method according to claim 8 wherein the niobate is selected from the group consisting of $Ba(NbO_3)_2$ and $Cd(NbO_3)_2$.

13. A method according to claim 8 wherein the slowly dissolving salt added to the solution is a silver salt.

14. A method according to claim 13 wherein the silver salt is a silver halide.

15. A method according to claim 13 wherein the silver salt is AgCN.

16. A method according to claim 13 wherein the silver salt is $AgIO_3$.

17. A method according to claim 8 wherein the slowly dissolving salt added to the solution is $Mn_2(CO)_{10}$.

18. A method according to claim 8 wherein the oxide is a heavy metal oxide.

19. A method according to claim 18 wherein the heavy metal oxide selected from the group consisting of is $ZrO_2$ and $TiO_2$.

20. A method according to claim 8 wherein the dye is selected from the group consisting of copper pthallocyanine and zinc pthallocyanine.

21. A method according to claim 1 wherein the concentration of the solids in said film does not exceed 50% by weight of cellulose.

22. A method according to claim 1 wherein a softener is added to the solution.

23. A method according to claim 21 wherein the softener is glycerol.

24. A method according to claim 22 wherein the softener is decane.

25. A method according to claim 1 wherein the casting step is conducted at ambient temperature.

26. A method according to claim 1 wherein casting of the film is effected by direct application of a water stream to the solution.

27. A method according to claim 25 wherein the casting step is performed at a relative humidity of 35–80% and a temperature range of 15–30 degrees Celsius.

28. A method according to claim 1 wherein the rinsing step involves the application of water to the film.

29. A method according to claim 28 wherein the rinsing step involves the use of a water/alcohol mixture in which the alcohol does not exceed a 50% by volume ratio.

30. A method according to claim 1 wherein the drying step involves air drying.

31. A method according to claim 1 wherein the drying step involves vacuum drying.

32. A method according to claim 1 wherein the drying step involves press-drying.

* * * * *